United States Patent [19]
Lapin et al.

[11] Patent Number: 6,147,226
[45] Date of Patent: Nov. 14, 2000

[54] SYNTHESIS OF CYCLOPENTYL 2-THIENYL KETONE, TILETAMINE AND TILETAMINE ACID ADDITION SALTS, SUCH AS TILETAMINE HYDROCHLORIDE

[75] Inventors: Yuri Aleksandrovich Lapin, West Lafayette; Ignacio H. Sanchez, Lafayette, both of Ind.

[73] Assignee: Great Lakes Chemical Corporation, West Lafayette, Ind.

[21] Appl. No.: 09/481,563

[22] Filed: Jan. 11, 2000

Related U.S. Application Data

[63] Continuation-in-part of application No. 09/250,369, Feb. 16, 1999, abandoned.

[51] Int. Cl.$^7$ .................................................. C07D 333/22
[52] U.S. Cl. ............................................. 549/70; 549/75
[58] Field of Search .................................................. 549/70

[56] References Cited

U.S. PATENT DOCUMENTS

| 3,522,273 | 7/1970 | Parcell | 260/332.3 |
|---|---|---|---|
| 5,034,400 | 7/1991 | Olney | 514/315 |
| 5,235,068 | 8/1993 | Minai et al. | 548/540 |
| 5,597,832 | 1/1997 | Michaelides et al. | 514/285 |
| 5,616,580 | 4/1997 | Olney | 514/226.2 |
| 5,648,087 | 7/1997 | Ovaert et al. | 424/423 |

FOREIGN PATENT DOCUMENTS

| 2 518 999 | 1/1983 | France . |
|---|---|---|
| 09 031010 | 4/1997 | Japan . |

OTHER PUBLICATIONS

Clerici, F., et al., "N–Arylsulfonylamidines: Part 2. A New Synthesis of Ketones from N'–Tosylamidines and Organolithium Compounds", *Synthesis* Nov. 1987, pp. 1025–1027.

Jur'ew, Yu K., et al., *Zh. Obshch–Khim* 26 (1956), pp. 3341–3344.

M. Wierzbicki et al.: "Amino Derivatives of Phenyl Alkyl Thiophene as Inhibitors of Bone Resorption" ARZNEIM. FORSCH., vol. 48, No. 8, 1998, pp. 840–849, XP000910137 * p. 841, right–hand column.

H. D. Hartough, A. I. Kosak: "Acylation Studies in the Thiophene and Furan Series. VI. Direct Acylation With Carboxylic Acids and Phosphorus Pentoxide" J. AMER. CHEM. SOC., vol. 69, No. 10, 1947, pp. 3098–3099. XP000909843 * table I.

Snyder, H.R., et al., "Polyphosphoric Acid As Reagent In Organic Chemistry. VII. Acylation", *Journal of American Chemical Society*, vol. 77, Jan. 20, 1955, pp. 364–366.

*Primary Examiner*—Bernard Dentz
*Attorney, Agent, or Firm*—Marshall, O'Toole, Gerstein, Murray & Borun

[57] ABSTRACT

A water-scavenging solvent, such a polyphosphoric acid, can be used for the synthesis of cyclopentyl 2-thienyl ketone by the direct acylation of cyclopentanecarboxylic acid without first reacting the cyclopentanecarboxylic acid with thionylchloride to form the acid chloride, while achieving new and unexpected yields. A tiletamine-free base can be made from the cyclopentyl 2-thienyl ketone with a halide in the presence of a solvent for the cyclopentyl 2-thienyl ketone to form a halogenated cyclopentane 2-thienyl ketone, aminating the halogenated cyclopentane 2-thienyl ketone by reaction with an amine, and subjecting the reaction product to thermal rearrangement, in a suitable solvent, and at a sufficient temperature to form tiletamine free base. Each step for the formation of tiletamine free base can be accomplished using the same solvent, e.g., dichlorobenzene so that intermediates need not be isolated between reactions.

51 Claims, No Drawings

SYNTHESIS OF CYCLOPENTYL 2-THIENYL KETONE, TILETAMINE AND TILETAMINE ACID ADDITION SALTS, SUCH AS TILETAMINE HYDROCHLORIDE

CROSS-REFERENCE TO RELATED APPLICATION

This application is a continuation-in-part of application Ser. No. 09/250,369, filed Feb. 16, 1999 now abandoned.

BACKGROUND OF THE INVENTION

1. Field of the Invention

The present invention is directed to an improved method of making cyclopentyl 2-thienyl ketone, tiletamine and tiletamine acid addition salts, such as tiletamine hydrochloride.

2. Description of the Prior Art

U.S. Pat. No. 3,522,273 ('273) discloses a method of making tiletamine, or 2-amino-2-(2-thienyl)cyclohexanone, and tiletamine acid addition salts, such as the hydrochloride.

As disclosed in the '273 patent, there are two routes to the synthesis of tiletamine hydrochloride, based on cyclopentyl 2-thienyl ketone (Scheme 1) or tetrahydro-2-pyranyl ether of cyclopentanone cyanohydrin (Scheme 2) as starting compounds, as follows:

Scheme 1:

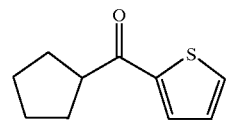

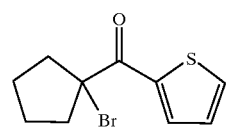

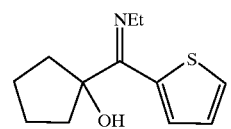

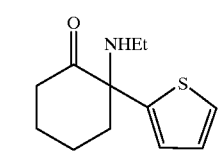

Scheme 2:

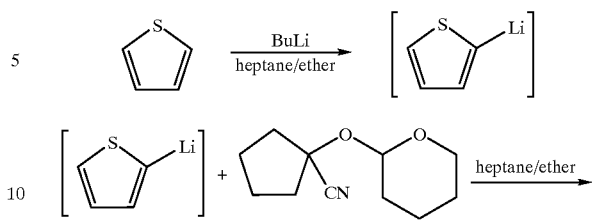

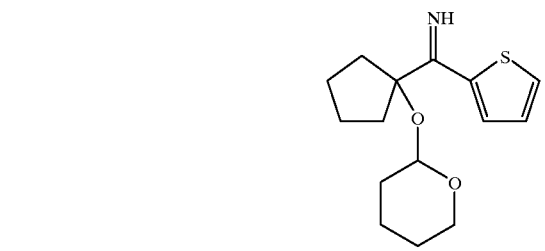

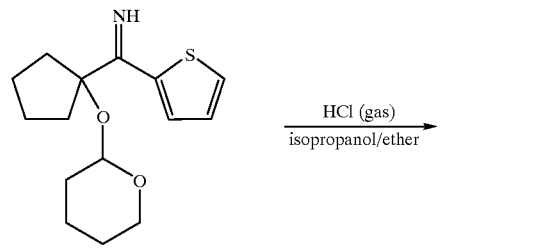

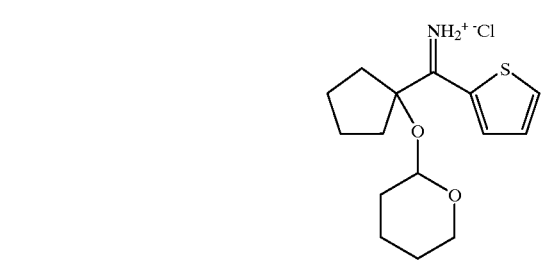

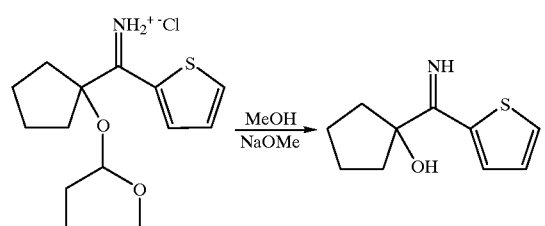

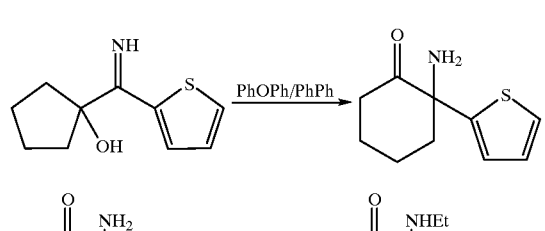

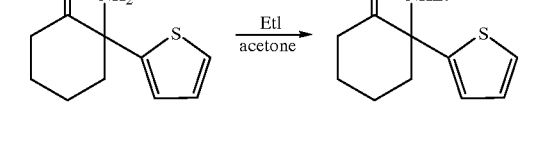

-continued

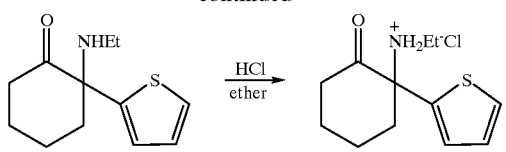

Due to availability of the starting compound, lower number of separate steps, lower raw material and operational costs, Scheme 1 is more promising than Scheme 2. However, both Schemes have several shortcomings. First, each step of the synthesis requires a different solvent. Multiple solvents complicate the post-reaction work-up, isolation and solvent recovery steps, and add significantly to the manufacturing cost of the process. In addition, solvents such as carbon tetrachloride and ether are restricted solvents. Moreover, ether is difficult to recover industrially and highly flammable. Second, the processes typically call for multiple isolations and purifications of the intermediates, which substantially affects the operational cost of commercial manufacture.

Cyclopentyl 2-thienyl ketone has been prepared by the Friedel-Crafts reaction of thiophene with initially preformed cyclopentanecarboxylic acid chloride (Scheme 3), as disclosed in U.S. Pat. No. 5,597,832 or with tetracyclopentylcarboxysilane (Scheme 4), *Jur'ew, Yu K., et al. Zh. Obshch-Khim.*, 26, 1956 3341–3344:

Scheme 3 (Example 33a of 5,597,832):

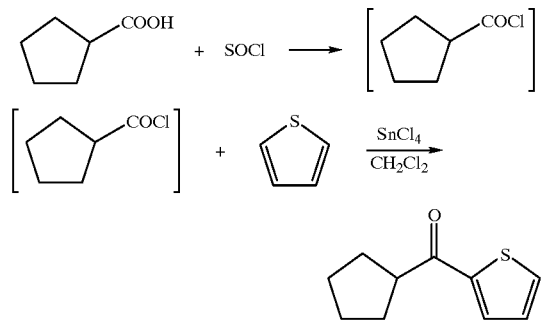

Scheme 4:

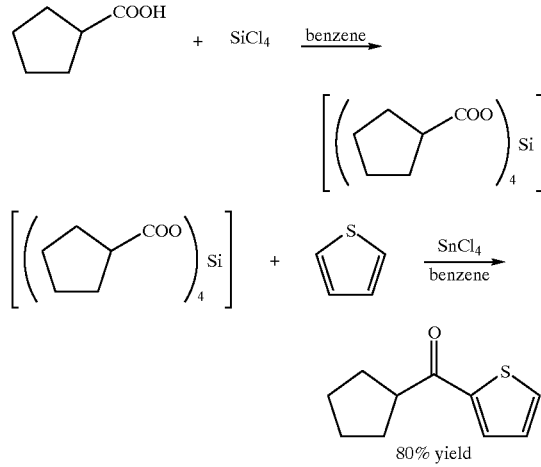

80% yield

Both Schemes 3 and 4 have the same major shortcoming- stannic chloride is used as a catalyst for the Friedel-Crafts reaction. In addition to its cost, stannic chloride introduces a heavy metal contamination to the process waste stream which is a major problem during manufacture.

It is also known, that cyclopentyl 2-thienyl ketone can be prepared from N'-tosylcyclopentylamidine by reaction with 2-thienyl lithium (Scheme 5), see Clerici, F. et al. *Synthesis*, 11, 1987, 1025–1027:

Scheme 5:

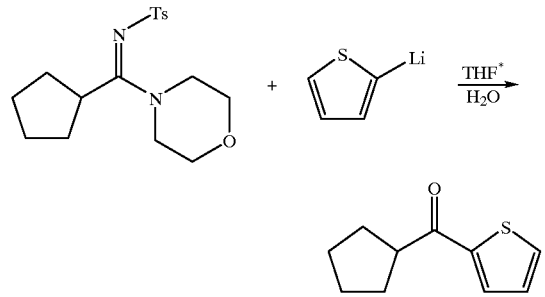

63% yield

* tetrahydrofuran

This Scheme 5 approach has some scientific interest, but is not desirable from a commercial production standpoint.

In accordance with the present invention, we have discovered alternatives to the original acylation routes to synthesize cyclopentyl 2-thienyl ketone. It has been found that cyclopentanecarboxylic acid can be directly reacted with thiophene, without first forming the cyclopentanecarboxylic acid chloride, using a water scavenging solvent, such as polyphosphoric acid, at unexpectedly high yields, to avoid the stannic chloride (heavy metal) waste stream contamination. In accordance with a preferred embodiment of the present invention, polyphosphoric acid is the water scavenging solvent of choice for the Friedel-Crafts reaction of cyclopentanecarboxylic acid and thiophene (Scheme 6).

As shown in the prior art method of Scheme 3, the prior art reaction requires first forming the acid chloride, requires a tin-containing catalyst, such as a stannic chloride, and methylene chloride as a solvent for the reaction of cyclopentanecarboxylic acid chloride with thiophene to form cyclopentyl 2-thienyl ketone. In accordance with the present invention, the synthesis of cyclopentyl 2-thienyl ketone, in accordance with the following reaction, can be achieved by directly reacting cyclopentanecarboxylic acid with thiophene in polyphosphoric acid.

Scheme 6 (direct acylation of thiopene with cyclopentanecarboxylic acid):

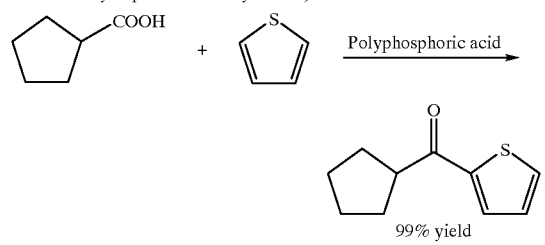

99% yield

In comparison with published procedures for the preparation of cyclopentyl 2-thienyl ketone, this approach has the following advantages:
1. This route is the most direct and bypasses the formation of the acid chloride,
2. Polyphosphoric acid plays role both a solvent and a reagent, which is a water scavenger, and
3. It eliminates the need to use thionyl chloride (a reagent for acid chloride formation) or tetrachlorosilane (for a synthesis of organosilyl derivative) and stannic chloride (a catalyst for the Friedel-Crafts reaction).

As disclosed in Snyder, Elston, J. Amer. Chem Soc: 77, 1955, 364, polyphosphoric acid was used in a reaction of thiophene and acetic acid, using about 5 times more polyphosphoric acid than the amount found effective in accordance with the present invention. To achieve the full advantage of the present invention, the above Scheme 6 reaction is carried out using a weight ratio of water-scavenging solvent, e.g., polyphosphoric acid, to thiophene of less than about 10:1, preferably less than about 8:1, more preferably less than about 5:1, and most preferably less than about 2.3:1 to avoid or lessen polyphosphoric acid waste water disposal problems (see Minai, et al. U.S. Pat. No. 5,235,068) while providing unexpected yields. To achieve the full advantage of the present invention, the weight ratio of water-scavenging solvent, e.g., polyphosphoric acid, to thiophene should be at least 1:1, preferably at least 1.5:1, more preferably at least 2:1.

In accordance with the preferred embodiment of the above reaction, a three component mixture was stirred at 75° C. for 2 hours. Then, the reaction mixture was diluted with water and extracted with o-dichlorobenzene to afford 99% pure product (GC, area % analysis). The mixture was azeotropically dried by stripping a small portion of the solvent. The crude mixture was submitted to the next step (Scheme 7). Halogenation (bromination) of the crude cyclopentyl 2-thienyl ketone at room temperature (Scheme 7) gave the corresponding α-halogenated ketone with a high purity, usually 97–99% by GC, area % analysis.

Scheme 7 (bromination):

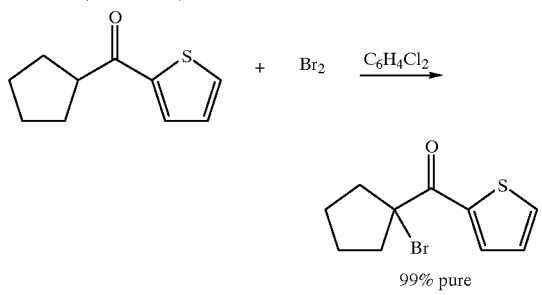

99% pure

A work up procedure after the bromination step is a simple evaporation of the solvent, which can be collected and recycled to any step of the process. Evaporation of the o-dichlorobenzene removes residual hydrogen bromide as well. A crude material, without any purification, was carried through directly to the next amination step. A 75% wt/wt solution of α-bromoketone in o-dichlorobenzene was used to prevent solidification of the starting material during amine addition. The amination reaction resulted in 96% pure (GC, area % analysis) product (Scheme 8).

Scheme 8 (amination):

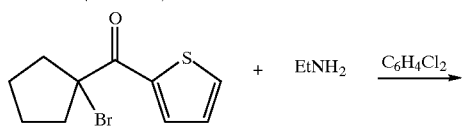

-continued

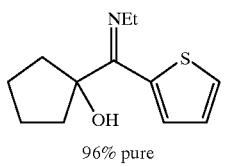

96% pure

An excess of ethylamine, used in the reaction, was evaporated from the reaction mixture under mild vacuum, and the ethylamine was recovered and recycled. An ethylamine hydrobromide salt by-product was washed out with water. A solution of crude 1-hydroxycyclopentyl 2'-thienyl N-ethyl ketimine in o-dichlorobenzene was refluxed for 1.5 hours at a temperature of at least about 100° C., preferably about 180° C. to about 230° C., e.g. 220° C. to 225° C., to produce 90% pure (GC, area % analysis) tiletamine free base by the thermal rearrangement reaction shown in Scheme 9.

Scheme 9 (thermal rearrangement):

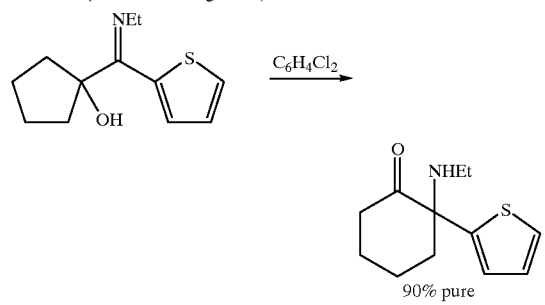

90% pure

The single solvent strategy, after formation of cyclopentyl 2-thienyl ketone, as shown in Schemes 7, 8 and 9, and the capability of transferring a crude reaction mixture through all steps 6, 7, 8 and 9, without isolation of the intermediates resulted in up to 70% yield (based on cyclopentanecarboxylic acid) of tiletamine free base. The conversion of tiletamine to its hydrochloride salt in o-dichlorobenzene at this stage allows for the use of only a single solvent throughout the entire process. However, a reaction of hydrogen chloride gas with tiletamine in o-dichlorobenzene was found to result in conversion of only about 39% of the available free base to the hydrochloride salt. Therefore, a different solvent was used for the final step. In the prior art method diethyl ether was the solvent of choice for this step, but diethyl ether is flammable and very difficult to handle. We have found that the use of di-n-butyl ether or t-butyl methyl ether and HCl gas result in the complete conversion of tiletamine to the corresponding hydrochloride salt, as shown in the acid addition salt reaction of Scheme 10.

Scheme 10 (acid addition salt reaction):

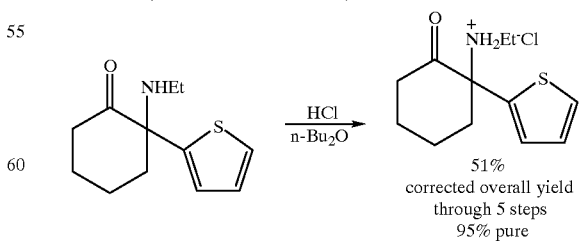

51%
corrected overall yield
through 5 steps
95% pure

The above-described synthesis of cyclopentyl 2-thienyl ketone, tiletamine and tiletamine acid addition salts has the following distinct advantages:

1. Tiletamine and its hydrochloride salt are produced with high yield.
2. The multi-solvent process can be replaced by a procedure, employing only one solvent for the synthesis of tiletamine free base from cyclopentyl 2-thienyl ketone—two solvents for good yields of tiletamine acid addition salts, involving a second solvent only at the acid addition salt step of the process.
3. A crude reaction mixture can be carried through five steps while avoiding complicated work ups, isolations, and purifications of the intermediates.

EXAMPLES

Example 1

Cyclopentyl 2-thienyl ketone synthesis
Direct acylation of thiophene with cyclopentanecarboxylic acid A solution of 8.8 g (105 mmol, 1.2 equivs.) of thiophene and 10.0 g (88 mmol) of cyclopentanecarboxylic acid in 20 g of polyphosphoric acid was stirred at 75° C. for 2 hours. The reaction mixture was diluted with water and extracted with o-dichlorobenzene to afford 99% pure product (GC, area % analysis). The mixture was azeotropically dried by stripping a small portion of the solvent. The crude cyclopentyl 2-thienyl ketone solution was then used without purification, for the bromination step of Example 2.

Example 2

1-Bromocyclopentyl 2'-thienyl ketone

Bromine (74.9 g, 468 66 mmol) was added for 30 min to a stirred solution of crude cyclopentyl 2'-thienyl ketone (438 mmol assumed, a reaction mixture from Example 1) in o-dichlorobenzene at room temperature. The reaction mixture was stirred for a further hour and concentrated under vacuum to leave an oily product, which was 99% pure (GC, area % analysis) 1-bromocyclopentyl 2'-thienyl ketone.

Example 3

1-Hydroxycyclopentyl 2'-thienyl N-ethyl ketimine

Ethylamine (8.2 g, 181.35 mmol, 4.7 equivs.) was condensed in a flask, which had an attached dry ice condenser. The crude α-bromoketone (38.58 mmol assumed) from Example 2 was then added slowly over 1 hour, keeping the temperature at approximately 0° C. After a further 2 hours of stirring, the reaction mixture was allowed to warm to room temperature for another 2 hours. The remaining ethylamine was evaporated under mild vacuum. An excess of ethylamine, removed from the reaction mixture, was recovered and recycled. The reaction mixture was diluted with 25 mL of o-dichlorobenzene and quickly washed with cool water to remove the ethylamine hydrobromide salt, which was formed as a by-product in the reaction. The reaction mixture was dried by stripping a small portion of the solvent under vacuum. The solution, containing crude 1-hydroxycyclopentyl 2'-thienyl N-ethyl ketimine (96% pure by GC, area % analysis) in o-dichlorobenzene, was used, without isolation, for the thermal rearrangement reaction in Example 4.

Example 4

2-Ethylamine-2-(2'-thienyl)cyclohexanone (tiletamine) thermal rearrangement reaction A solution of crude I -hydroxycyclopentyl 2'-thienyl N-ethyl ketimine (38 58 mmol assumed) in 25 mL of o-dichlorobenzene, from Example 3, was refluxed for 1.5 hours at 180° C. to synthesize 90% pure (GC, area % analysis) tiletamine free base, by thermal rearrangement.

Example 5

2-Ethylamino-2(2'-thienyl)cyclohexanone hydrochloride (tiletamine hydrochloride)

a. o-Dichlorobenzene as a solvent for the acid addition salt reaction

Hydrogen chloride gas (2 81 g, 77.16 mmol) was bubbled through a solution of tiletamine (38.58 mmol assumed—the mixture from Example 4) in o-dichlorobenzene, keeping the temperature at about 2° C. The resulting reaction mixture was filtered to produce 3.6 grams of a yellow solid. This solid was vigorously stirred for 30 min in 15 mL of acetone. The mixture was filtered, the solid reaction product was washed with acetone and dried at 40° C. giving 2.3 g of tiletamine hydrochloride (23% overall process yield through five steps, 99.93% pure by RP-IPC area % analysis). The filtrate and acetone wash were combined and subjected to evaporation to recover 4.47 g (36% corrected yield, 70% pure by GC area % analysis) of unreacted free tiletamine.

b. Di-n-butyl ether as a solvent for the acid addition salt reaction

Hydrogen chloride gas (2.81 g, 77.16 mmol) is bubbled through a solution of tiletamine (38.58 mmol assumed—the mixture from Example 4) in di-n-butyl ether, keeping the temperature at about 2° C. The resulting reaction mixture is filtered to produce about 8.0 grams of a yellow solid. This solid is vigorously stirred for 30 min in 30 mL of acetone. The mixture is filtered, to remove the solid reaction product, the reaction product is washed with acetone and dried at 40° C. giving about 7.0 g of tiletamine hydrochloride.

c. Di-n-butyl ether as a solvent for the acid addition salt reaction of mixed reactants Hydrogen chloride gas (2.81 g, 77.16 mmol) was bubbled through a solution of a 7:1 mixture (molar ratio) of tiletamine and 1-hydroxycyclopentyl 2'-thienyl N-ethyl ketimine in di-n-butyl ether, as might be a typical mixture from the thermal rearrangement reaction of 1-hydroxycyclopentyl 2'-thienyl N-ethyl ketimine (38.58 mmol assumed) (Scheme 9) carried out in di-n-butyl ether, at 5° C. The resulting solid was filtered, washed with di-n-butyl ether and stirred vigorously for 0.5 hour in acetone. The solid was filtered, washed with acetone and dried at 40° C. to afford 5.4 g (95% pure by HPLC, area % analysis, 51% overall process yield through six steps) The filtrate and washed solutions were combined and subjected to evaporation to recover 1.8 g (19% corrected yield, 92% pure by GC area % analysis) unreacted 1-hydroxycyclopentyl 2'-thienyl N-ethyl ketimine.

What is claimed is:

1. A method of reacting cyclopentanecarboxylic acid with thiophene to produce cyclopentyl 2-thienyl ketone comprising contacting the cyclopentanecarboxylic acid with thiophene in the presence of a water-scavenging solvent, in a weight ratio of water-scavenging solvent to thiophene of less than about 10:1.
2. The method of claim 1, wherein the water-scavenging solvent is polyphosphoric acid.
3. The method of claim 1, wherein the weight ratio of water-scavenging solvent to thiophene is less than about 8 1.
4. The method of claim 3, wherein the weight ratio of water-scavenging solvent to thiophene is less than about 5:1.
5. The method of claim 4, wherein the weight ratio of water-scavenging solvent to thiophene is less than about 2.3:1.

6. The method of claim 3, wherein the weight ratio of water-scavenging solvent to thiophene is at least 1:1.

7. The method of claim 6, wherein the weight ratio of water-scavenging solvent to thiophene is at least 2:1.

8. The method of claim 1, wherein after the reaction of cyclopentanecarboxylic acid with thiophene to form the cyclopentane 2-thienyl ketone, the cyclopentane 2-thienyl ketone is dried and then reacted with a halide in the presence of a solvent for the cyclopentane 2-thienyl ketone to form a halogenated cyclopentane 2-thienyl ketone.

9. The method of claim 8, wherein the solvent added for the halide reaction is selected from the group consisting of chlorobenzene, dichlorobenzene, dichloroethane, and mixtures thereof.

10. The method of claim 9, wherein the solvent is dichlorobenzene.

11. The method of claim 10, wherein the solvent is o-dichlorobenzene.

12. The method of claim 1, further comprising forming a tiletamine free base from the cyclopentyl 2-thienyl ketone by sequentially (a) contacting the cyclopentyl 2-thienyl ketone with a halide in the presence of a solvent for the cyclopentyl 2-thienyl ketone to form a halogenated cyclopentane 2-thienyl ketone, (b) aminating the halogenated cyclopentane 2-thienyl ketone by reaction with an amine; and (c) subjecting the reaction product of step (b) to thermal rearrangement, in a suitable solvent, and at a sufficient temperature to form tiletamine free base.

13. The method of claim 12, wherein steps (a), (b), and (c) are carried out in the presence of the same solvent.

14. The method of claim 13, wherein the solvent is dichlorobenzene.

15. The method of claim 12, wherein the step (b) is achieved by adding an amine to the reaction mixture resulting from step (a), without first separating the halogenated cyclopentane 2-thienyl ketone from the reaction mixture.

16. The method of claim 15, wherein the halogenated cyclopentane 2-thienyl ketone reacts with ethylamine to form 1-hydroxycyclopentyl 2'-thienyl N-ethyl ketimine.

17. The method of claim 15, wherein step (c) is achieved by heating the reaction mixture resulting from step (b) without first separating the reaction product from step (b) from the reaction mixture.

18. The method of claim 17, wherein heating at a temperature sufficient for thermal rearrangement is accomplished by refluxing the reaction mixture at a temperature sufficient to vaporize the solvent.

19. The method of claim 18, wherein the boiling point of the solvent used in the thermal rearrangement reaction is at least 100° C.

20. The method of claim 12, further including the step of making an acid addition salt from the tiletamine free base by reacting the tiletamine free base with gaseous hydrogen halide in the presence of a solvent for the tiletamine free base.

21. The method of claim 20, wherein the solvent for the tiletamine free base is selected from the group consisting of chlorobenzene, dichlorobenzene, di-n-butyl ether, t-butyl methyl ether, and mixtures thereof.

22. The method of claim 21, wherein the solvent for the tiletamine free base is dichlorobenzene.

23. The method of claim 22, wherein the solvent for the tiletamine free base is o-dichlorobenzene.

24. The method of claim 21, wherein the solvent for the tiletamine free base is selected from the group consisting of di-n-butyl ether, t-butyl methyl ether, and mixtures thereof.

25. The method of claim 24, wherein the solvent for the tiletamine free base is di-n-butyl ether.

26. A method of reacting cyclopentanecarboxylic acid with thiophene to produce cyclopentyl 2-thienyl ketone comprising contacting the cyclopentanecarboxylic acid with thiophene in the presence of a water-scavenging solvent.

27. The method of claim 26, wherein the water-scavenging solvent is polyphosphoric acid.

28. The method of claim 26, wherein after the reaction of cyclopentanecarboxylic acid with thiophene to form the cyclopentane 2-thienyl ketone, the cyclopentane 2-thienyl ketone is dried and then reacted with a halide in the presence of a solvent for the cyclopentane 2-thienyl ketone to form a halogenated cyclopentane 2-thienyl ketone.

29. The method of claim 28, wherein the solvent added for the halide reaction is selected from the group consisting of chlorobenzene, dichlorobenzene, dichloroethane, and mixtures thereof.

30. The method of claim 29, wherein the solvent is dichlorobenzene.

31. The method of claim 30, wherein the solvent is o-dichlorobenzene.

32. The method of claim 26, further comprising forming a tiletamine free base from the cyclopentyl 2-thienyl ketone by sequentially (a) contacting the cyclopentyl 2-thienyl ketone with a halide in the presence of a solvent for the cyclopentyl 2-thienyl ketone to form a halogenated cyclopentane 2-thienyl ketone; (b) aminating the halogenated cyclopentane 2-thienyl ketone by reaction with an amine; and (c) subjecting the reaction product of step (b) to thermal rearrangement, in a suitable solvent, and at a sufficient temperature to form tiletamine free base.

33. The method of claim 32, further including the step of making an acid addition salt from the tiletamine free base by reacting the tiletamine free base with gaseous hydrogen halide in the presence of a solvent for the tiletamine free base.

34. The method of claim 33, wherein the solvent for the tiletamine free base is selected from the group consisting of chlorobenzene, dichlorobenzene, di-n-butyl ether, t-butyl methyl ether, and mixtures thereof.

35. The method of claim 34, wherein the solvent for the tiletamine free base is dichlorobenzene.

36. The method of claim 35, wherein the solvent for the tiletamine free base is o-dichlorobenzene.

37. The method of claim 34, wherein the solvent for the tiletamine free base is selected from the group consisting of di-n-butyl ether, t-butyl methyl ether, and mixtures thereof.

38. The method of claim 37, wherein the solvent for the tiletamine free base is di-n-butyl ether.

39. A method of reacting cyclopentanecarboxylic acid with thiophene to produce cyclopentyl 2-thienyl ketone comprising contacting the cyclopentanecarboxylic acid with thiophene in the presence of a water-scavenging solvent and thereafter forming a tiletamine free base from the cyclopentyl 2-thienyl ketone by sequentially (a) contacting the cyclopentyl 2-thienyl ketone with a halide in the presence of a solvent for the cyclopentyl 2-thienyl ketone to form a halogenated cyclopentane 2-thienyl ketone; (b) aminating the halogenated cyclopentane 2-thienyl ketone by reaction with an amine; and (c) subjecting the reaction product of step (b) to thermal rearrangement, in a suitable solvent, and at a sufficient temperature to form tiletamine free base, wherein steps (a), (b) and (c) are carried out in the presence of the same solvent.

40. The method of claim 39, wherein the solvent is dichlorobenzene.

41. The method of claim 39, wherein the step (b) is achieved by adding an amine to the reaction mixture resulting from step (a), without first separating the halogenated cyclopentane 2-thienyl ketone from the reaction mixture.

42. The method of claim 41, wherein the halogenated cyclopentane 2-thienyl ketone reacts with ethylamine to form 1-hydroxycyclopentyl 2'-thienyl N-ethyl ketimine.

43. The method of claim 41, wherein step (c) is achieved by heating the reaction mixture resulting from stop (b) without first separating the reaction product from step (b) from the reaction mixture.

44. The method of claim 43, wherein heating at a temperature sufficient for thermal rearrangement is accomplished by refluxing the reaction mixture at a temperature sufficient to vaporize the solvent.

45. The method of claim 44, wherein the boiling point of the solvent used in the thermal rearrangement reaction is at least 100° C.

46. The method of claim 39, further including the step of making an acid addition salt from the tiletamine free base by reacting the tiletamine free base with gaseous hydrogen halide in the presence of a solvent for the tiletamine free base.

47. The method of claim 46, wherein the solvent for the tiletamine free base is selected from the group consisting of chlorobenzene, dichlorobenzene, di-n-butyl ether, t-butyl methyl ether, and mixtures thereof.

48. The method of claim 47, wherein the solvent for the tiletamine free base is dichlorobenzene.

49. The method of claim 48, wherein the solvent for the tiletamine free base is o-dichlorobenzene.

50. The method of claim 27, wherein the solvent for the tiletamine free base is selected from the group consisting of di-n-butyl ether, t-butyl methyl ether, and mixtures thereof.

51. The method of claim 50, wherein the solvent for the tiletamine free base is di-n-butyl ether.

* * * * *

UNITED STATES PATENT AND TRADEMARK OFFICE
CERTIFICATE OF CORRECTION

PATENT NO. : 6,147,226
DATED : November 14, 2000
INVENTOR(S) : Lapin et al.

It is certified that error appears in the above-identified patent and that said Letters Patent is hereby corrected as shown below:

Column 11,
Line 7, replace "stop" with -- step --.

Signed and Sealed this

Twenty-third Day of April, 2002

Attest:

JAMES E. ROGAN
*Director of the United States Patent and Trademark Office*

*Attesting Officer*